(12) United States Patent
Miller et al.

(10) Patent No.: US 11,382,639 B2
(45) Date of Patent: Jul. 12, 2022

(54) MEDICAL DRIVE UNIT OF THE HANDHELD TYPE WITH SENSOR DEVICE AND KICKBACK CONTROL

(71) Applicant: Aesculap AG, Tuttlingen (DE)

(72) Inventors: Simon Miller, Deißlingen (DE); Robin Andris, Obereschach (DE); Tom Fesenmeyer, Villingen-Schwenningen (DE)

(73) Assignee: AESCULAP AG, Tuttlingen (DE)

( * ) Notice: Subject to any disclaimer, the term of this patent is extended or adjusted under 35 U.S.C. 154(b) by 115 days.

(21) Appl. No.: 16/984,657

(22) Filed: Aug. 4, 2020

(65) Prior Publication Data

US 2021/0038232 A1 Feb. 11, 2021

(30) Foreign Application Priority Data

Aug. 5, 2019 (DE) ...................... 10 2019 121 121.2

(51) Int. Cl.
*A61B 17/16* (2006.01)
*A61B 17/14* (2006.01)
*A61B 17/00* (2006.01)

(52) U.S. Cl.
CPC ........ *A61B 17/1628* (2013.01); *A61B 17/142* (2016.11); *A61B 2017/00398* (2013.01);
(Continued)

(58) Field of Classification Search
CPC . A61B 17/16; A61B 17/1613; A61B 17/1622; A61B 17/1624; A61B 17/1626;
(Continued)

(56) References Cited

U.S. PATENT DOCUMENTS 4,871,003 A    10/1989  Lucas et al.
6,033,409 A *   3/2000  Allotta ............... A61B 17/1622
                                                  606/170
(Continued)

FOREIGN PATENT DOCUMENTS

EP           2449986 A1    5/2012
WO      2009032314 A1    3/2009
(Continued)

OTHER PUBLICATIONS

German Search Report received in Application No. 10 2019 121 121.2 dated Apr. 2, 2020, 14 pages.
(Continued)

*Primary Examiner* — Eric S Gibson
(74) *Attorney, Agent, or Firm* — Culhane Meadows, PLLC; Christopher A. Rothe

(57) ABSTRACT

A medical drive unit receives and rotationally drives a medical, preferably surgical tool, by a motor, preferably an electric motor, housed in the drive unit which can be operated via a control or regulation unit. The medical drive unit includes a sensor device for directly or indirectly detecting or determining a movement of the drive unit or a holding movement of the user which is triggered by the motor corresponding to the power applied to the tool and a kickback control which automatically effects a reduction of the driving power or turning off of the motor upon detection of a predetermined drive unit or holding movement or a predetermined drive-unit or holding-movement amount.

9 Claims, 2 Drawing Sheets

Figure 1:
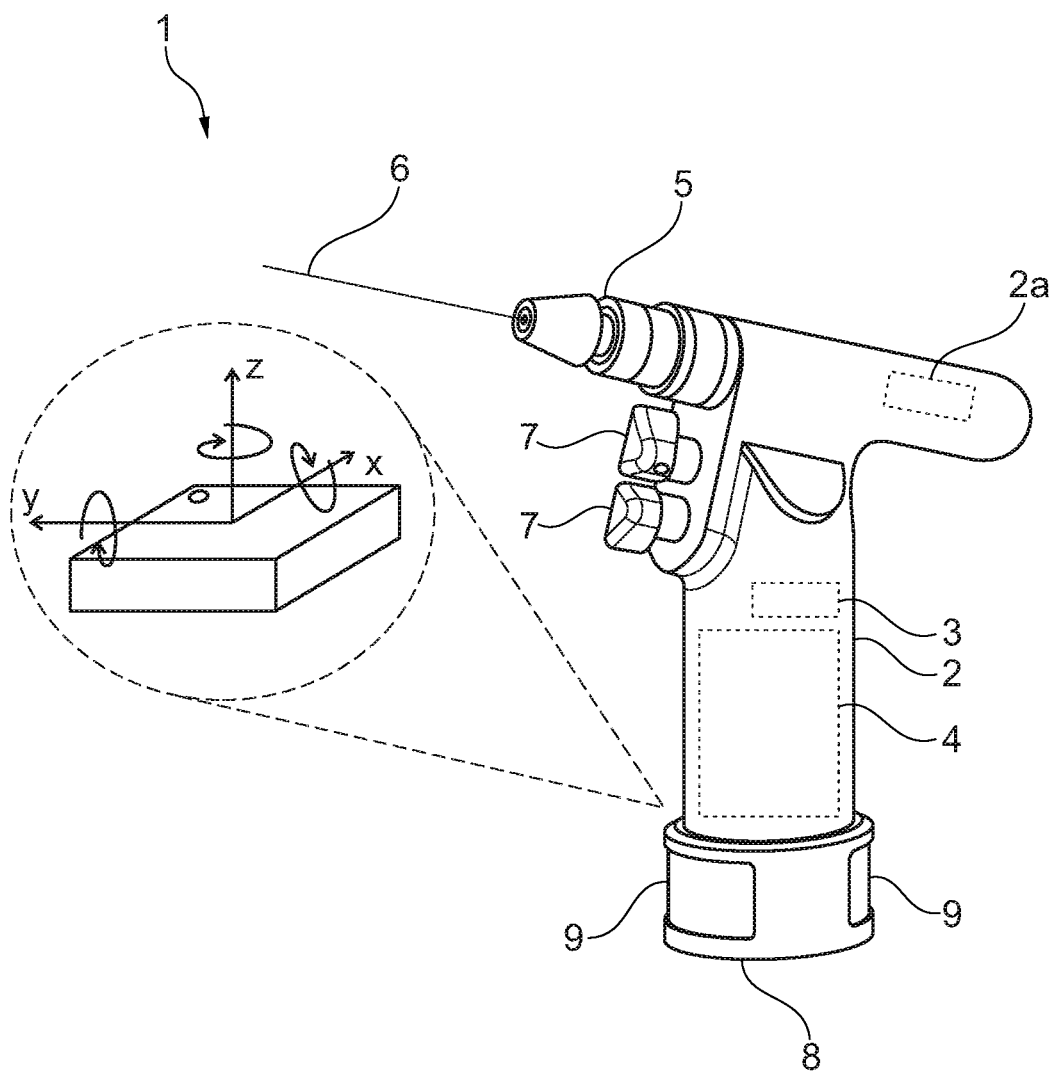

(52) U.S. Cl.
CPC ............... *A61B 2017/00424* (2013.01); *A61B 2017/1602* (2013.01); *A61B 2562/0219* (2013.01)

(58) Field of Classification Search
CPC ............ A61B 17/1628; A61B 17/1659; A61B 2017/00398; A61B 2017/1602; A61B 2034/2048; A61B 2090/031; A61B 2090/066; A61B 2562/0219
See application file for complete search history.

(56) References Cited

U.S. PATENT DOCUMENTS

| | | | | |
|---|---|---|---|---|
| 7,638,958 | B2* | 12/2009 | Philipp | A61B 17/1622 318/139 |
| 7,681,659 | B2* | 3/2010 | Zhang | B25B 21/00 173/1 |
| 8,511,945 | B2* | 8/2013 | Apkarian | A61B 17/1626 408/1 R |
| 8,529,567 | B2* | 9/2013 | Garcia | A61B 17/16 606/80 |
| 8,821,493 | B2* | 9/2014 | Anderson | A61B 90/06 606/80 |
| 8,894,654 | B2* | 11/2014 | Anderson | A61B 17/17 606/80 |
| 8,926,614 | B2* | 1/2015 | Hsieh | A61B 17/1626 606/80 |
| 9,204,885 | B2* | 12/2015 | McGinley | A61B 17/1615 |
| 9,877,734 | B2* | 1/2018 | Anderson | B25B 23/0064 |
| 10,245,043 | B2* | 4/2019 | Xie | A61B 90/03 |
| 10,736,643 | B2* | 8/2020 | Anderson | G01L 3/08 |
| 11,154,307 | B2* | 10/2021 | Chiang | A61B 17/1626 |
| 2005/0116673 | A1* | 6/2005 | Carl | A61B 17/1626 318/432 |
| 2005/0131415 | A1* | 6/2005 | Hearn | A61B 17/8875 606/80 |
| 2006/0241628 | A1* | 10/2006 | Parak | A61B 17/1626 606/80 |
| 2007/0084613 | A1* | 4/2007 | Zhang | B25F 5/001 173/1 |
| 2008/0077149 | A1* | 3/2008 | Hoegerle | A61B 17/1626 606/80 |
| 2008/0245159 | A1* | 10/2008 | Garshelis | H02J 7/0042 73/862.27 |
| 2009/0245956 | A1* | 10/2009 | Apkarian | A61B 34/30 408/1 R |
| 2009/0326537 | A1* | 12/2009 | Anderson | A61B 17/17 606/80 |
| 2011/0245833 | A1* | 10/2011 | Anderson | B25B 23/0064 606/80 |
| 2011/0301611 | A1* | 12/2011 | Garcia | B25B 21/002 606/80 |
| 2012/0310247 | A1* | 12/2012 | Hsieh | A61B 17/1626 606/80 |
| 2014/0166323 | A1 | 6/2014 | Cooper | |
| 2014/0216773 | A1* | 8/2014 | Steurer | B23Q 11/0092 173/1 |
| 2014/0371752 | A1* | 12/2014 | Anderson | A61B 17/1633 606/80 |
| 2015/0080966 | A1* | 3/2015 | Anderson | A61B 17/1628 606/280 |
| 2016/0089154 | A1* | 3/2016 | Chien | A61B 17/1626 606/79 |
| 2016/0128704 | A1* | 5/2016 | McGinley | A61B 17/1626 606/80 |
| 2017/0202607 | A1 | 7/2017 | Shelton, IV et al. | |
| 2017/0231644 | A1* | 8/2017 | Anderson | A61B 90/06 606/80 |
| 2018/0140308 | A1* | 5/2018 | Anderson | B25B 23/0064 |
| 2019/0029697 | A1* | 1/2019 | Anderson | A61B 17/1633 |
| 2019/0247057 | A1* | 8/2019 | Anderson | B25B 23/0064 |
| 2021/0038232 | A1* | 2/2021 | Miller | A61B 17/142 |
| 2021/0059649 | A1* | 3/2021 | Hunt | A61B 17/1626 |
| 2021/0085342 | A1* | 3/2021 | Ayer | A61B 17/1626 |
| 2021/0378684 | A1* | 12/2021 | Lambert | A61B 17/1622 |

FOREIGN PATENT DOCUMENTS

| | | |
|---|---|---|
| WO | 2017139674 A1 | 8/2017 |
| WO | 2019035088 A1 | 2/2019 |
| WO | 2019141536 A1 | 7/2019 |

OTHER PUBLICATIONS

Extended European Search Report received in Application No. 20189463.1-1122 dated Jan. 15, 2021, 10 pages.

* cited by examiner

MEDICAL DRIVE UNIT OF THE HANDHELD TYPE WITH SENSOR DEVICE AND KICKBACK CONTROL

CROSS-REFERENCE TO RELATED APPLICATION(S)

This application claims the benefit of priority under 35 U.S.C. § 119 of German Application No. 10 2019 121 121.2, filed Aug. 5, 2019, the content of which is incorporated by reference herein in its entirety.

FIELD

The present disclosure relates to a medical drive unit of the handheld/grip type for receiving and rotationally driving of a medical tool in the field of operative surgery.

BACKGROUND

Basically, surgery is concerned with the surgical treatment of diseases and injuries, wherein various specialist areas such as vascular surgery or orthopedics and accident surgery are categorized. Common to all specialist areas is the use of a variety of medical instruments to realize a surgery. What medical instruments are ultimately used depends on the location and type of procedure, and on the function of the medical instrument to be used.

In most surgical procedures in the field of surgery, instruments such as scalpels, scissors or forceps are used to cut, prepare and hold tissue. However, in orthopedics and accident surgery, which focus on the surgical treatment of diseases and injuries of the musculoskeletal system, various drive units such as surgical drills, saws or milling machines are often required in addition to the standard medical instruments in the course of a surgery in order to be able to process bones appropriately, for example.

Especially in osteosynthesis, which generally combines several different surgical procedures for the treatment of fractured/broken or otherwise damaged bones with the aim of restoring the full functionality of the affected bone as quickly as possible, such drive units are nowadays of great importance and regularly in use.

For example, in order to adequately treat a fractured bone, osteosynthesis involves repositioning the individual fragments of the affected bone to their original shape/position and stabilizing them accordingly. In order to stabilize the bone, drive units such as surgical drills or milling machines are used to drill or mill holes in selected areas of the affected bone to provide it with drill channels. Depending on the procedure, corresponding implants such as screws are then inserted into these drill channels to fix the affected bone.

During the application of such surgical drive units on the patient, however, it can happen that the rotatable surgical tool clamped to the medical drive unit becomes jammed/obstructed in the patient's bone. As a result, rotational energy is generated by the medical drive unit in the direction of the user, which dissipates on the user. The reason for this often lies in the control of the motor of the medical drive unit. For example, if the motor of the medical drive unit is operated via a slider which is speed-controlled, the torque of the hand-held medical drive unit is not limited, so that at a certain point the force applied to the medical drive unit by the user is no longer sufficient and the user loses control of the medical drive unit.

The rotation of the drive unit in the movement direction of the clamped tool resulting from this loss of control by the user, which is also referred to as the knock-back movement of the medical drive unit, can lead to injuries to the user, especially in the arm area and the wrist and shoulder joints as well as to injuries to the patient, which in turn can influence the course of the surgery.

From the prior art, medical drive units of the handheld type are known for receiving surgical tools, which are intended to ensure that the preceding application-related disadvantages are avoided by means of torque limiting.

Such a medical drive unit provides integrated torque limiting which is based on an increase in current as a function of time. If the medical drive unit experiences a steep rise in current within a certain time, this is attributed to jamming or movement of the drive unit in the direction of rotation of the clamped tool.

However, no direct jamming of the tool or movement of the medical drive unit out of control of the user is detected/determined in the case of such torque limiting. Instead, only exceeding of a maximum torque set before the application is detected by detecting the speed of current change (di/dt). A maximum torque set prior to an application can furthermore restrict the user in his application of the medical drive unit, since the maximum torque cannot be adapted to the conditions that may change during the application. Furthermore, the realization of the precedingly described torque limiting in connection with the requirements for a medical device, for example with regard to reprocessing processes, is rather difficult. Finally, there is the possibility that the drive unit may be used by different persons during a surgical procedure, who may develop different physical strengths. This means that the maximum torque set in advance, if applicable, may be too low or at least acceptable for one person to safely hold the drive unit, while for the other person the maximum torque is set too high, which may cause the drive unit to make uncontrolled movements in this person's holding hand when this maximum torque is approached. In order to avoid this critical, i.e. uncontrolled, movement situation, the maximum permissible torque would have to be reset each time the drive unit is handed over from one person to another, which is very time-consuming and unreliable.

SUMMARY

In view of the precedingly stated problem, the basic object of the present disclosure is providing a medical drive unit, preferably of the hand grip/handheld type, which allows smooth application of the medical drive unit in order to avoid injuries and losing control of the application of the user and to thereby make the whole course of the surgery significantly safer.

The core idea of the present disclosure is therefore not to or not only to detect/monitor/control a possibly adjustable maximum permissible torque on the tool, as it is suggested in the prior art, but (as sole or additional measure) to provide a movement detection unit, for example a yaw sensor, detecting/determining movements of the drive unit (for example hand held in which the drive unit/motor is built in) or respectively holding movements of the operator (preferably triggered by the drive unit) and a controller (ECU) connected to the movement detection unit and being adapted to draw conclusions from the detected movements or respectively movement amounts about the current movement situation and thus indirectly about the torque/force applied by the drive unit holding means or the holding hand of the operator by the drive unit and, based on this, to raise and/or decrease the drive, accordingly.

In other words, exceeding the maximum holding force that can be applied by an operator will inevitably cause so-called yielding/shaking (reaction movements) of the holding hand and thus a corresponding (uncontrolled) movement of the drive unit. If this yielding/shaking of the holding hand is detected/recognized, it can be concluded that the drive torque is too high for the current operator and the drive unit it therefore controlled to be turned down. This makes the handling of such a controlled drive unit safer and also saves the need to save several different maximum torques for different operators.

In concrete terms, a medical drive unit of the handheld type is provided, which is designed to receive a medical, preferably surgical, tool (drill, milling cutter, etc.) and to operate it in a rotatable manner with a motor, and which is provided according to the invention with a sensor device/unit which either directly or indirectly detects/determines a movement of the drive unit or a holding movement of a user, wherein the sensor device is triggered by the power output from the motor to the tool. Moreover, it is advantageous if the medical drive unit of the handheld type in combination with the sensor device comprises an integrated kickback control unit (feedback control unit) which automatically effects a reduction of the (current) driving power and/or turning off of the motor upon detection of a predetermined drive unit or holding movement or a drive-unit or holding-movement amount.

According to a further aspect of the disclosure, it is advantageous to design/provide the sensor device as inertial sensor and preferably as gyroscope and/or acceleration sensor in order to be able to detect a movement of the medical drive unit in die movement direction of the tool clamped in the medical drive unit via three axes (X, Y, Z). The movements of the medical drive unit may be rotational movement or directional movement, wherein the first option is triggered, for example, by a drill (milling cutter, acetabulum, screwdriver) and the latter may be triggered, for example, by a sagittal saw or jigsaw.

If jamming or a tendency for jamming of the medical drive unit occurs during application this causes a rise in torque, due to which the drive unit moves in the movement direction of the clamped tool when the counterforce of the holder/user. In the light of this, according to an aspect of the invention, the medical drive unit is provided comprising an electronic evaluation system which detects/determines based on the rate of change of the movement of the medical drive unit in the movement direction of the tool clamped in the medical drive unit, whether there is an increased torque.

Another aspect involves providing a medical drive unit of the handheld type, according to which the inertial sensor and the electronic evaluation system are integrated in an accumulator, preferably in an accumulator head, which furthermore preferably is removably, if applicable, inserted in a (hand) grip of the drive unit. By means of such an arrangement or addition of the accumulator and the possibility to remove and/or exchange the accumulator of the medical drive unit and correspondingly also the inertial sensor and the electronic evaluation system, it is possible to continue to meet the requirements for medical devices, for example with regard to reprocessing processes. Furthermore, this has a positive effect on the service life and operating costs of the medical drive unit, and enables a relatively simple realization of the system, since the inertial sensor is implemented/integrated into an already existing control system.

For a constructive implementation of the disclosed principle it is advantageous, in contrast to the prior art, to disregard a configuration of the torque before application of the medical drive unit. This allows that the torque limiting of the medical drive unit of the handheld type does not require any external computing unit or data storage/evaluation and functions autonomously without additional devices and wireless or wired communication.

According to another aspect of the disclosure, it is furthermore provided to customize torque limiting of the medical drive unit by the control or regulation unit to the application and the user in a permanently adaptable manner, wherein a torque of the medical drive unit is adapted by the control or regulation unit to the maximum torque usable by the user in order to avoid occurrence of an excessive torque for the user in the course of the application.

In other words, the provided controller or regulation unit has an (additional) self-learn unit//learning tool, which identifies, for the respective, preferably current application and/or the respective, preferably current user, the respective (individual) torque (for example in the course of one application) at which a drive unit movement/drive unit acceleration (or hand movement/hand acceleration) generated/induced by the drive unit (as a result of the currently occurring torque at the tool) reaches/exceeds a (pre-)determined amount and (temporarily) sets this identified torque as the (currently) maximum permissible torque.

In the further course of the application, the torque input of the drive unit into the tool is limited in such a way (for example by setting a friction clutch between drive and tool) that this maximum permissible torque is then not exceeded anymore.

In this way, for example, the (currently) maximum permissible torque can not only be associated with a specific user and/or a specific application, but it could, for example also adapt to the current constitution of the user, i.e. to the progressing fatigue of the user, wherein the torque load of the gradually tiring user (continuously) decreases. The latter could technically be achieved, despite having set the maximum permissible torque at the beginning, by repeatedly detecting the current movement acceleration amounts, for example, by closely timed measurement cycles, and then comparing the amounts to the (pre-)determined amount and then correspondingly verifying (if applicable reducing) the current, maximum permissible torque (feed-back-control).

Alternatively, it is also possible, for example, to save an average fatigue curve along which the current, maximum permissible torque is changed (reduced) without any further measurement cycles (feed-forward-control).

A length of the torque limiting of the medical drive unit depends, according to a further aspect of the disclosure, on the time needed by the user for stabilizing the medical drive unit.

Finally, another aspect of the disclosure relates to the motor housed in the medical drive unit which is provided as a commutated electric motor. According to another aspect, it is advantageous if the kickback control automatically effects, upon detection of a predetermined holding movement or a predetermined holding movement amount, turning off and/or decelerating and/or driving the motor in the reverse direction.

At this point, it is explicitly noted that the preceding aspects can solve the stated object individually as well as in any combination and are therefore intended to be claimable individually or in any combination within the scope of this application.

BRIEF DESCRIPTION OF THE DRAWING FIGURES

Figure 2:
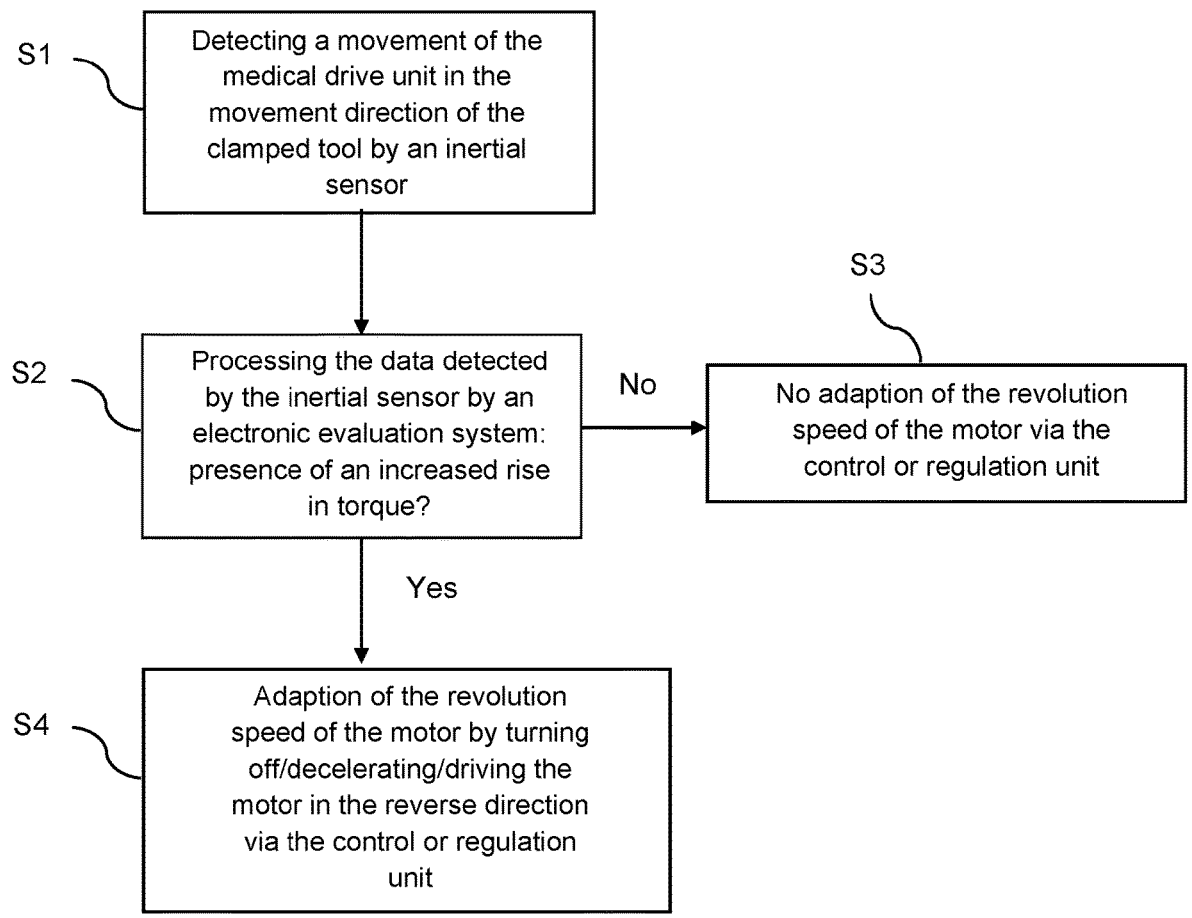

FIG. 1 shows a side view of a medical drive unit of the handheld type to illustrate a system structure according to an embodiment of the disclosure, and FIG. 2 shows a flowchart for a schematic process of realizing a kickback control according to the embodiment example shown in FIG. 1.

DETAILED DESCRIPTION

FIG. 1 shows an embodiment of a medical drive unit 1 (medical instrument) of the handheld type, comprising a grip 2, a motor 2a, a sensor device and an electronic evaluation system 3 (these are shown in FIG. 1 as a unit, but may also be separate units), an accumulator 4, a gear attachment 5, which is designed as a drilling gear attachment, a medical tool 6, which is clamped in the gear attachment 5 and designed as a drilling tool, two operating elements 7, a cover panel/a cover 8 and two cover-panel release buttons 9.

The sensor device 3 indicated in FIG. 1, which is designed in the form of an inertial sensor, and preferably as a gyroscope and/or acceleration sensor, and which detects a movement of the medical drive unit 1 via three axes, as well as the electronic evaluation system (control/regulation device) 3 required to evaluate the data detected by the sensor device 3 are provided inside the grip 2 below an accumulator 4 indicated in FIG. 1 or directly in the accumulator head. The accumulator 4 located inside the grip 2 is designed in such a way that it can be removed, e.g. for replacement or for reprocessing processes of the medical drive unit 1, by removing the cover panel 8 from the grip 2.

A control or regulation unit, which is not shown in FIG. 1 or only together with the sensor unit 3, for operating the motor 2a, is provided in the accumulator head or within the grip 2. Moreover, the motor 2a indicated in FIG. 1, which is formed as a commutated electric motor and is supplied with electric power from the accumulator 4, is housed inside the medical drive unit 1. Such an arrangement of the individual components has the advantage that the medical drive unit 1 can function autonomously without further devices and wireless or wired communication Generally, the medical drive unit 1 is powered by power/force generated by the motor 2a, wherein the power of the motor 2a can be regulated via the control or regulation unit. Via a clutch not shown in FIG. 1, the power generated by the electric motor is transferred to the gear attachment 5. The power of the electric motor transmitted from the clutch is in turn converted into a torque by the gear integrated in the gear attachment 5, wherein this torque is used to rotationally drive the clamped medical tool 6 formed as drilling tool in FIG. 1.

The grip 2 of the medical drive unit 1 is ergonomically designed, wherein the grip 2 has a cylindrical handpiece and a bulge at a distal end of the grip 2 for placing the thumb of the hand used by the user to control the medical drive unit 1. At the distal end, the grip 2 integrally merges into a cigar-shaped extension extending in a transverse direction of the grip 2. The diameter of the cigar-shaped extension is smaller than the diameter of the cylindrical handpiece of the grip 2 and is sufficient to accommodate the motor 2a.

At a distal end of the cigar-shaped extension, the gear attachment 5 is clamped in or supported in the medical drive unit 1, wherein the gear attachment 5 can be exchanged depending on the application. In the gear attachment 5, depending on the gear attachment type, a suitable medical tool 6 (drilling machine, milling cutter, etc.) is clamped which can also be exchanged.

The two operating elements 7 are provided in a distal area (facing the patient) of the cylindrical handpiece of the grip 2. By actuating the operating elements 7 by the user, the medical tool 6 clamped in the gear attachment 5 of the medical drive unit 1 is activated/operated. The operating elements 7 can be configured with regard to various parameters which may be useful for the operation of medical tool 6 clamped in the gear attachment 5 of the medical drive unit 1, such as the direction of rotation or the speed of rotation.

At a proximal end of the grip 2 (facing the user), the cover panel 8 is provided in the form of a cap, which closes the medical drive unit 1 at a front side of the cylindrical handpiece of the grip 2. Two cover-panel release buttons 9 are integrated in the cover panel 8, the actuation of which enables the cover panel 8 to be removed.

FIG. 2 shows a flow diagram for a schematic course of realizing a kickback control according to the embodiment shown in FIG. 1.

If the medical drilling/milling machine 1 shown in FIG. 1 is used, for example, during a hip surgery, the user has to apply very great force to scrape out the hip joint (the hip-joint socket) due to the large contact surface and strength of the hip bone in order to prevent the medical drilling/milling machine 1 from rotating in the movement direction of the acetabulum tool 6 clamped in the medical drilling/milling machine 1.

It is noted at this point that the tool 6 in FIG. 1 is only shown symbolically as a line and does not represent the concrete form of the actually currently used tool 6.

During such an application (e.g. milling), torque peaks are to be expected as a result of jamming or a jamming tendency of the tool 6, wherein these torque peaks are passed into the medical drive unit 1 and from there into the user's holding hand/arm. Accordingly, the inertial sensor 3, which is preferably designed as a gyroscope and/or acceleration sensor, detects in step S1 preferably permanently/closely timed over three axes (X, Y, Z) a movement/acceleration of the medical drilling/milling machine 1 in particular in the movement direction of the acetabulum tool 6 clamped in the medical drilling/milling machine 1.

The electronic evaluation system 3 connected to the inertial sensor 3 processes in step S2 the movement data or acceleration data of the medical drilling/milling machine 1 and determines, for example, based on the rate of change of the detected movement data/acceleration data of the medical drilling/milling machine 1, whether an increased/excessive torque is present or whether the torque currently applied to the tool 6 is too high or can be compensated by the person holding it. If the electronic evaluation system 3 determines that there is no increased rise in torque or no increased torque, i.e. the medical drilling/milling machine 1 can be held steadily by the person, in step S3 a control or regulation unit does not adapt the revolution speed of the motor 2a and/or the torque of the acetabulum tool 6 clamped in the medical drilling/milling machine 1, so that the acetabulum tool 6 clamped in the medical drilling/milling machine 1 is operated with the same torque or, if applicable, increasing torque. If the electronic evaluation system 3 detects, however, an increased/excessive rise in torque or a torque which is too high, i.e. the medical drilling/milling machine 1 cannot be held steadily by the person, in step S4 the electronic evaluation system/control or regulation unit 3 adapts the revolution speed of the motor 2a and/or of the acetabulum tool 6 clamped in the medical drilling/milling machine 1, so that the acetabulum tool 6 clamped in the medical drilling/milling machine 1 is operated with a changed/corrected torque. Adapting/reducing the revolution speed/the torque of the motor 2a can be realized by turning off and/or decelerating and/or driving the motor 2a in the reverse direction or by changing the torque-transmission capability of the clutch (adjustable friction clutch) between the motor 2a and the gear attachment 5.

According to the present disclosure, it is furthermore provided that the electronic evaluation system/control or regulation unit 3 is capable of learning such that the control or regulation unit 3 maintains the already (initially) adapted revolution speed or the already (initially) adapted torque for the current application and/or the current user as the maximum permissible upper limit, which will not be exceeded during the further course of the application. In this way, an inadmissible movement/acceleration of the drive unit 1 as a result of an excessively high torque output, if applicable, can be prevented from the beginning.

Such a permanently variable torque limiting, i.e. continuously adapting to changing conditions (e.g. as a result of increased fatigue of the user)/automatic torque limiting, for the further application allows the user to operate the medical drilling machine 1 with the torque maximally possible for the user, so that the hip joint can be scraped out always with the maximum possible advance throughout the application, without having to make manual adjustments of the max. torque.

In summary, the invention consequently relates to a medical drive unit 1 of the handheld type for receiving and for rotationally driving a medical, preferably surgical tool 6, by means of a motor 2a, preferably an electric motor, housed in the drive unit 1 which can be operated via a control or regulation unit. According to the invention, such a medical drive unit 1 of the handheld type comprises a sensor device 3 for directly or indirectly detecting or determining a movement of the drive unit 1 or a holding movement of the user which is triggered by the motor 2a corresponding to the power applied to the tool 6 and a kickback control which automatically effects a reduction of the driving power or turning off of the motor 2a upon detection of a predetermined drive unit or holding movement or a predetermined drive-unit or holding-movement amount.

The invention claimed is:

1. A medical drive unit for receiving and rotatingly driving of a medical tool by a motor housed in the medical drive unit and operable by a controller or regulation unit, comprising a sensor device directly or indirectly detecting or determining a movement or acceleration of the medical drive unit or a holding movement or holding acceleration of a user, which is triggered by the motor corresponding to its power applied to the medical tool and having a kickback control unit or tool, which automatically reduces a driving power or turns off the motor upon detection of a predetermined medical drive unit or holding movement or acceleration, or a predetermined medical drive unit or holding movement or acceleration amount, the controller or regulation unit having a learning unit or tool, which is adapted to identify an individual torque for a current application and/or the user at which the kickback control unit reduces the driving power or turns off the motor, the learning unit or tool also being adapted to limit the medical drive unit for the current application and/or the user to the individual torque as a maximum permissible future torque, wherein the learning unit or tool maintains the driving power and continuously adapts the maximum permissible future torque to changing conditions of the current application and/or the user.

2. The medical drive unit of claim 1, wherein the sensor device is one of an inertial sensor and an acceleration sensor, which detects, via three axes, a movement of the medical drive unit in a movement direction of the medical tool.

3. The medical drive unit of claim 2, wherein the controller or regulation unit determines based on a rate of change of the movement of the medical drive unit in the movement direction of the medical tool whether an increased torque input or an increased rise in torque is present.

4. The medical drive unit of claim 2, wherein said one of an inertial sensor and an acceleration sensor and the controller or regulation unit are integrated in a grip of the medical drive unit or in an accumulator, which is further removably inserted in the grip of the medical drive unit.

5. The medical drive unit of claim 1, wherein a torque limiting of the medical drive unit is customized to the current application and the user in a permanently adaptable manner by the controller or regulation unit, wherein a torque of the medical drive unit is continuously adapted by the controller or regulation unit to the maximum permissible future torque to avoid an occurrence of excessive torque for the user during the application.

6. The medical drive unit of claim 5, wherein a length or duration of the torque limiting of the medical drive unit depends on a time which the user needs for stabilizing the medical drive unit.

7. The medical drive unit of claim 1, wherein the motor is a commutated electric motor.

8. The medical drive unit of claim 1, wherein the kickback control unit or tool automatically effects turning off and/or decelerating and/or driving the motor in a reverse direction and/or a change in a torque-transmission capability of a gear connected downstream of the motor upon detection of the predetermined medical drive unit or holding movement or acceleration, or detection of a predetermined medical drive unit or holding movement or acceleration amount.

9. The medical drive unit of claim 1, wherein the learning unit or tool is adapted to compare a detected medical drive unit or holding movement or acceleration to the predetermined medical drive unit or holding movement or acceleration and to verify the maximum permissible future torque.

* * * * *